United States Patent [19]

Pennetreau

[11] Patent Number: 5,107,016
[45] Date of Patent: Apr. 21, 1992

[54] PROCESS FOR THE PREPARATION OF β-HYDROXYBUTYRIC ACID ESTERS

[75] Inventor: Pascal Pennetreau, La Hulpe, Belgium

[73] Assignee: Solvay & Cie (Société Anonyme), Brussels, Belgium

[21] Appl. No.: 460,236

[22] Filed: Jan. 2, 1990

[30] Foreign Application Priority Data

Jan. 6, 1989 [FR] France .................................. 89 00243

[51] Int. Cl.$^5$ ............................................ C07C 69/66
[52] U.S. Cl. .................................................... 560/179
[58] Field of Search ......................................... 560/179

[56] References Cited

U.S. PATENT DOCUMENTS 2,526,554  7/1947  Gresham et al. .................... 560/179

FOREIGN PATENT DOCUMENTS 0046017  2/1982  European Pat. Off. .
2822472 12/1978  Fed. Rep. of Germany .
2369242  5/1978  France .

OTHER PUBLICATIONS

"Helvetica Chimica Acta", vol. 65, No. 49, 1982, pp. 495–503.
The Merck Index, Tenth Edition, pp. 1230 and 1232, published by Merck & Co., Inc., (1983).

*Primary Examiner*—Bruce Gray
*Attorney, Agent, or Firm*—Spencer & Frank

[57] ABSTRACT

Process for the preparation of β-hydroxybutyric acid esters, comprising:
1) a step involving alcoholysis of the polyhydroxybutyrate in the presence of an alcohol, a halogenated solvent, and an acid,
2) a neutralization step comprising the addition of an alcoholate in solution in the alcohol,
3) a purification step comprising the addition of a halogenated solvent and the azeotropic removal of water and the alcohol,
4) a step for recovery of the ester, comprising a filtration, a distillation of the halogenated solvent and a distillation of the ester.

This process enables β-hydroxybutyric acid esters of high purity to be obtained.

8 Claims, No Drawings

PROCESS FOR THE PREPARATION OF β-HYDROXYBUTYRIC ACID ESTERS

The present invention relates to a process for the preparation of β-hydroxybutyric acid esters by alcoholysis of poly-β-hydroxybutyrate.

A process for the preparation of β-hydroxybutyric acid esters has already been proposed in the document Helvetica Chim Acta 1982, 65 (2), p. 495–503. This process comprises a step involving alcoholysis of polyhydroxybutyrate, which may or may not be isolated from the biomass, with the aid of methanol and sulphuric acid in the presence of a solvent such as 1,2-dichloroethane, a neutralization step by washings with an aqueous solution of NaCl and an aqueous solution of $NaHCO_3$ and then a purification step comprising drying over magnesium sulphate, filtration under reduced pressure and distillation. The washing steps in such a process lead to mixtures which are not easy to separate by settling, in particular because of the presence of two phases, an aqueous phase and an organic phase, which leads to the formation of emulsions Moreover, the reaction time, the separation time and the settling time are very long.

The aim of the present invention is to provide a process which does not have the drawbacks of this prior process.

To this end, the present invention relates to a process for the preparation of β-hydroxybutyric acid esters from poly-β-hydroxybutyrate, comprising:

a) a first step in which an alcoholysis of the poly-β-hydroxybutyrate is carried out in a medium comprising a homogeneous liquid phase of an alcohol, a halogenated solvent and an acid, b) a second step in which the acid is neutralized with a base soluble in the homogeneous liquid phase, c) a third step in which a halogenated solvent is added to the medium and the water formed and the alcohol are removed by azeotropic distillation, and d) a fourth step in which the ester formed is recovered.

The poly-β-hydroxybutyrate which can be treated according to the invention can be obtained in various ways. Numerous microorganisms, in particular bacteria, are capable of synthesizing it. The selection of the microorganisms is in general made on the basis of the relative amount of poly-β-hydroxybutyrate contained in the microorganism and as a function of the speed of growth of the microorganism and its rate of synthesis of poly-β-hydroxybutyrate.

These microorganisms can be treated directly, after separation and subsequent drying of the culture medium, to effect the alcoholysis of the poly-β-hydroxybutyrate without prior extraction of the poly-β-hydroxybutyrate. This separation can be effected by all means known to this end. One method of proceeding consists in centrifuging the culture medium so as to separate the microorganisms from the medium, washing the microorganisms with water and subsequently drying the microorganisms.

Another technique, described in European Patent 0,168,095, consists in extracting the poly-β-hydroxybutyrate from an aqueous suspension of microorganisms using a solvent which forms an azeotrope at least with the water, the water being removed by an azeotropic route.

Another technique consists in treating the microorganisms with a solution of sodium hypochlorite in order to obtain a poly-β-hydroxybutyrate which no longer contains cellular debris and in then drying the product obtained.

The alcohol used in the first step is chosen according to the type of ester which it is desired to prepare. Any type of alcohol may be used in the process according to the invention. In general, the process is carried out using aliphatic alcohols containing from 1 to 4 carbon atoms and more particularly using methanol, ethanol and propanol. Finally, good results have been obtained, in particular, with methanol and ethanol.

When methanol is used in the process, 0.1 to 50 ml of alcohol per g of poly-β-hydroxybutyrate is customarily used. Preferably, from 0.5 to 20 ml of alcohol per g of poly-β-hydroxybutyrate is used.

The halogenated solvents for the poly-β-hydroxybutyrate which are used in the first step are chosen from the solvents for poly-β-hydroxybutyrate which are miscible with alcohol and can be separated from the ester by distillation. Customarily, chloromethanes, chloroethanes and chloropropanes are used. In general, chloroform, 1,2-dichloroethane, 1,2-dichloropropane, 1,1,2-trichloroethane, 1,1,2,2-tetrachloroethane and 1,2,3-trichloropropane are used. Preferably, however, 1,2-dichloropropane or 1,2-dichloroethane is used. Finally, the solvent very particularly preferred is 1,2-dichloropropane.

When 1,2-dichloropropane is used as the halogenated solvent in the process of the invention, from 0.1 to 50 ml of 1,2-dichloropropane per g of poly-β-hydroxybutyrate, and preferably from 1 to 20 ml of 1,2-dichloropropane per g of poly-β-hydroxybutyrate, is used.

The acids used in the first step are those currently used in the prior art as an esterification catalyst. Sulphuric acid, p-toluenesulphonic acid and methanesulphonic acid are customarily used. Amongst these, good results have been obtained with sulphuric acid.

When sulphuric acid is used, amounts of between 1 and 5% by volume of concentrated acid in the alcohol, preferably from 2 to 4%, are customarily used.

In the process according to the invention, the reaction is carried out in a reaction mixture where the solvent, the alcohol, the acid and poly-β-hydroxybutyrate constitute only a single homogeneous liquid phase; the reaction mixture can, however, contain cellular debris and possibly undissolved poly-β-hydroxybutyrate, but whatever the case the reaction is carried out in the absence of a second liquid phase.

The temperature at which the first step of the process is carried out is between 25° and 160° C. It is preferably between 35° and 150° C.; good results have been obtained between 50° and 140° C.

The pressure at which the first step of the process is carried out is generally between 1 and 10 bars; it is customarily between 3 and 8 bars. Preferably, the reaction is carried out under autogenous pressure, which implies that the working pressure is fixed by the composition of the reaction mixture and by the temperature chosen.

The first step of the process according to the invention can be carried out in any equipment designed for this purpose.

During the second step of the process according to the invention, the acid is neutralized with a base which is a soluble in the homogeneous liquid phase and which forms with the acid a salt which precipitates at least partially from the mixture. Customarily an alkali metal alcoholate or alkaline earth metal alcoholate is used. Preferably, the alcoholate corresponding to the alcohol used in the first step is employed and sodium or potassium is used as the alkali metal or alkaline earth metal.

The addition of the base can be discontinuous. The neutralization is monitored by following the change in the mixture as a function of the coloration of a pH paper; the addition of base is stopped when the coloration of a pH paper corresponds to an acidity of between pH 5 and 6 in the aqueous phase.

Preferably, the base is used in solution in the same alcohol as that used in the first step.

The temperature at which the second step of the process is carried out is customarily between 20° and 50° C. and good results have been obtained at ambient temperature.

The pressure at which the second step of the process is carried out is between 1 and 3 bars: good results have been obtained at atmospheric pressure.

The second step of the process according to the invention can be carried out in any equipment designed for this purpose. Usually it is carried out in the equipment of the first step.

During the third step, a halogenated solvent is added to the mixture in order to remove the water formed, and in particular the alcohol, by azeotropic distillation.

The customary solvents for poly-β-hydroxybutyrate can be used as the halogenated solvent. In general, the chloromethanes, chloroethanes or chloropropanes are used, such as chloroform, 1,2-dichloroethane, 1,2-dichloropropane, 1,1,2,-trichloroethane, 1,1,2,2-tetrachloroethane and 1,2,3-trichloropropane. Preferably, a halogenated solvent identical to that used in the first step is employed. Accordingly, 1,2-dichloropropane is particularly preferably used in this step.

To effect the azeotropic removal, a volume of halogenated solvent equal to the expected volume of azeotrope is added to the mixture; this addition can be effected continuously before or during the distillation operation.

The azeotrope is removed under atmospheric pressure or under reduced pressure. The removal of the solvent is stopped when the temperature at the top reaches the boiling temperature of the pure solvent.

During the fourth step, the ester is recovered without further difficulty by any known technique, such as, in particular, filtration and/or centrifugation, followed by washing preferably carried out with a halogenated solvent identical to that used during the first or the third step, followed by a distillation of the halogenated solvent and a distillation of the β-hydroxybutyric acid ester.

The β-hydroxybutyric acid ester obtained by the process of the invention can be used in all the applications known for this product, that is to say in particular as a medicament, as an intermediate in the fine chemicals industry or as an additive in animal feeds.

The β-hydroxybutyric acid ester obtained according to the process of the invention can be used as such in chemical synthesis or can be hydrolysed with a view to obtaining β-hydroxybutyric acid with a minimum formation of crotonic acid.

The example which follows serves to illustrate the invention.

EXAMPLE 1

200 ml of 1,2-dichloropropane, 200 ml of methanol, 6 ml of concentrated sulphuric acid (0.110 mole of $H_2SO_4$) and 72 g of a culture of microorganisms which has been centrifuged, washed and then dried and which contains 60% of poly-β-hydroxybutyrate, which corresponds to 0.5 mole of $C_4$ units, are introduced, with stirring, into a 1-litre autoclave fitted with a manometer, a system for heating and controlling the temperature, a stirrer and a tube enabling samples to be taken.

The reactor is purged with nitrogen and the mixture is then heated at 110° C. for 5 hours. The pressure rises from 4.75 to 5 bars.

Heating is stopped and the reaction mixture is allowed to return to ambient temperature.

45 ml of a 1.3 M methanolic solution of sodium methylate are then added to the mixture; this addition neutralizes the sulphuric acid.

355 ml of 1,2-dichloropropane are then added to the mixture and azeotropic removal is carried out under atmospheric pressure; the boiling point of the azeotrope is 63° C.

The removal of 1,2-dichloropropane is stopped when the temperature reaches 96° C., the boiling point of 1,2-dichloropropane.

The mixture is then filtered through a frit plate of porosity P3 in 2 minutes and the residue is washed twice with 200 ml of 1,2-dichloropropane.

The filter cake is then dried under reduced pressure (<10 mm Hg) to constant weight. The filter cake has a moist weight of about 110 g and a final weight of about 45 g.

The 1,2-dichloropropane is removed under reduced pressure (<10 mm Hg) and the β-hydroxybutyric acid ester is then distilled under a pressure of 20 mm Hg. The boiling point of the methyl ester is 76° C. under 20 mm Hg.

50 g of virtually pure methyl β-hydroxybutyrate are obtained.

The ester contains very little methyl crotonate, of the order of 0.05 to 0.1 g/kg.

The distillation yields are 90%.

The 1,2-dichloropropane recovered during the distillation and washing operations is recycled in the process.

I claim:

1. Process for the preparation of β-hydroxybutyric acid esters from poly-β-hydroxybutyrate, characterized in that this process comprises:
   a) a first step in which an alcoholysis of the poly-β-hydroxybutyrate is carried out in a medium comprising a homogeneous liquid phase of an alcohol, a halogenated solvent and an acid,
   b) a second step in which the acid is neutralized with a alcoholate soluble in the homogeneous liquid phase,
   c) a third step in which a halogenated solvent is added to the medium and the water formed and the alcohol are removed by azeotropic distillation, and
   d) a fourth step in which the ester is recovered.

2. Process according to claim 1, characterized in that the alcoholate corresponds to the alcohol used in the first step.

3. Process according to claim 1 characterized in that the alcoholate is used in solution in the alcohol used in the first step.

4. Process according to any one of the preceding claim 1 characterized in that the fourth step comprises filtration and/or centrifugation.

5. Process according to claim 4, characterized in that the fourth step comprises a distillation of the ester.

6. Process according to claim 1 characterized in that the halogenated solvent used in the first step and in the third step is chosen, independently of one another, from the chloromethanes, the chloroethanes and the chloropropanes.

7. Process according to claim 6, characterized in that the halogenated solvent used in the first step and the halogenated solvent used in the third step are identical.

8. Process according to claim 7, characterized in that the halogenated solvent is 1,2-dichloropropane.

* * * * *